US012702839B2

(12) United States Patent
Shelton et al.

(10) Patent No.: US 12,702,839 B2
(45) Date of Patent: Aug. 11, 2026

(54) IMPLANTABLE MEDICAL DEVICE HAVING AN INERTIAL SENSING UNIT

(71) Applicant: The Alfred E. Mann Foundation for Scientific Research, Valencia, CA (US)

(72) Inventors: Brian Shelton, Ventura, CA (US); Brian Mech, Buffalo, MN (US); Sahar Elyahoodayan, Los Angeles, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 300 days.

(21) Appl. No.: 18/358,489

(22) Filed: Jul. 25, 2023

(65) Prior Publication Data

US 2024/0033524 A1 Feb. 1, 2024

Related U.S. Application Data

(60) Provisional application No. 63/392,291, filed on Jul. 26, 2022.

(51) Int. Cl.
*A61N 1/36* (2006.01)

(52) U.S. Cl.
CPC ..... *A61N 1/36139* (2013.01); *A61N 1/36171* (2013.01)

(58) Field of Classification Search
CPC ............ A61N 1/36139; A61N 1/36171; A61N 1/3601; A61N 1/36542; A61N 1/36578; A61N 1/0551
See application file for complete search history.

(56) References Cited

U.S. PATENT DOCUMENTS 5,345,824 A 9/1994 Sherman et al.
5,465,604 A 11/1995 Sherman
(Continued)

FOREIGN PATENT DOCUMENTS

EP 3184045 A1 6/2017

OTHER PUBLICATIONS

International Search Report and Written Opinion for International Application No. PCT/US2023/028576 dated Nov. 17, 2023, 17 pages.

(Continued)

*Primary Examiner* — Tammie K Marlen
(74) *Attorney, Agent, or Firm* — Lewis Roca Rothgerber Christie LLP

(57) ABSTRACT

A stimulation system configured to be implanted in a patient includes an implantable pulse generator (IPG) and an implantable lead system. The IPG includes a processor, a memory device, a power supply, and an inertial sensing unit configured to measure one or more physiological indicators of the patient. The implantable lead system includes at least one electrical lead coupled to the power supply and at least one electrode at a distal end of the electrical lead. The memory device includes instructions that cause the IPG to receive the physiological indicators within an initial range; increase the initial range to an enlarged range in response to the physiological indicators crossing a threshold maximum value or a threshold minimum value of the initial range; receive the physiological signals within the enlarged range, analyze the physiological indicators, and deliver stimulation to the patient through the electrode in response to the physiological indicators.

36 Claims, 4 Drawing Sheets

(56) References Cited

U.S. PATENT DOCUMENTS

| | | | | |
|---|---|---|---|---|
| 8,265,756 | B1 | 9/2012 | Snell et al. | |
| 9,398,859 | B2 | 7/2016 | Volpe et al. | |
| 2007/0027497 | A1 * | 2/2007 | Parnis | A61N 1/36114 607/45 |
| 2014/0358193 | A1 * | 12/2014 | Lyons | A61N 1/37229 607/48 |
| 2015/0157864 | A1 | 6/2015 | Rosenberg | |
| 2016/0091529 | A1 | 3/2016 | Dawson et al. | |
| 2016/0121110 | A1 | 5/2016 | Kent et al. | |
| 2018/0333578 | A1 | 11/2018 | Mock et al. | |
| 2021/0379381 | A1 | 12/2021 | Soin | |

OTHER PUBLICATIONS

Written Opinion of the International Preliminary Examining Authority for Application No. PCT/US2023/028576, mailed Mar. 13, 2024, 7 pages.

* cited by examiner

IMPLANTABLE MEDICAL DEVICE HAVING AN INERTIAL SENSING UNIT

CROSS-REFERENCE TO RELATED APPLICATION(S)

The present application claims priority to and the benefit of U.S. Provisional Patent Application No. 63/392,291, filed Jul. 26, 2022, entitled "Dynamic Accelerometer and Gyro Settings," the entire content of which is incorporated herein by reference.

BACKGROUND

1. Field

The present disclosure relates to implantable medical devices configured to determine physiological data of a patient with an inertial sensing unit.

2. Description of the Related Art

Implantable pulse generators (IPGs) are used for a variety of therapeutic treatments in a patient, such as neurostimulation, cardiac stimulation, and/or spinal cord stimulation. An implanted accelerometer and/or gyroscope in the IPG may be used to detect a patient's heart rate and respiration rate. The intensity of these detected signals may vary not only per patient but also per time of day. This is especially so for respiration detection wherein the intensity of the respiration signal will drop when a patient sleeps. Thus, it may be required to set the accelerometer and gyro to their most sensitive settings. Patient motion often results in a much stronger signal that will not only swamp the respiration or heart-rate signals but can also cause these sensors to hit their rails (i.e., maximum and minimum values). When the sensor output hits the rails, the output is non-linear and may be difficult if not impossible to filter out from the much lower respiration and heart rate signals that generally have different frequency components.

SUMMARY

The present disclosure relates to various embodiments of a stimulation system configured to be implanted in a patient. In one embodiment, the stimulation system includes an implantable pulse generator (IPG) and an implantable lead system. The IPG includes a processor, a memory device, a power supply, and an inertial sensing unit configured to measure physiological data such as one or more physiological indicators of the patient. The implantable lead system includes at least one electrical lead coupled to the power supply and at least one electrode at a distal end of the electrical lead. The memory device includes instructions that cause the IPG to receive the physiological indicators within an initial range; increase the initial range to an enlarged range in response to the physiological indicators crossing a threshold maximum value or a threshold minimum value of the initial range; receive the physiological indicators within the enlarged range, analyze the physiological indicators, and deliver stimulation to the patient through the electrode in response to the physiological indicators.

The present disclosure also relates to various embodiments of a method of providing stimulation to a patient for treatment of one or more medical conditions. In one embodiment, the method includes measuring, with an inertial sensing unit of an implantable pulse generator implanted in the patient, one or more physiological indicators of the patient within an initial range; increasing the initial range to an enlarged range in response to at least one of the physiological indicators crossing a threshold maximum value or a threshold minimum value of the initial range; receiving the one or more physiological indicators within the enlarged range; analyzing the one or more physiological indicators; and delivering stimulation to the patient, through at least one implantable lead coupled to the implantable pulse generator, in response to the one or more physiological indicators.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features or tasks may be combined with one or more other described features or tasks to provide a workable device or method.

BRIEF DESCRIPTION OF THE DRAWINGS

The features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

DETAILED DESCRIPTION

Figure 1A:
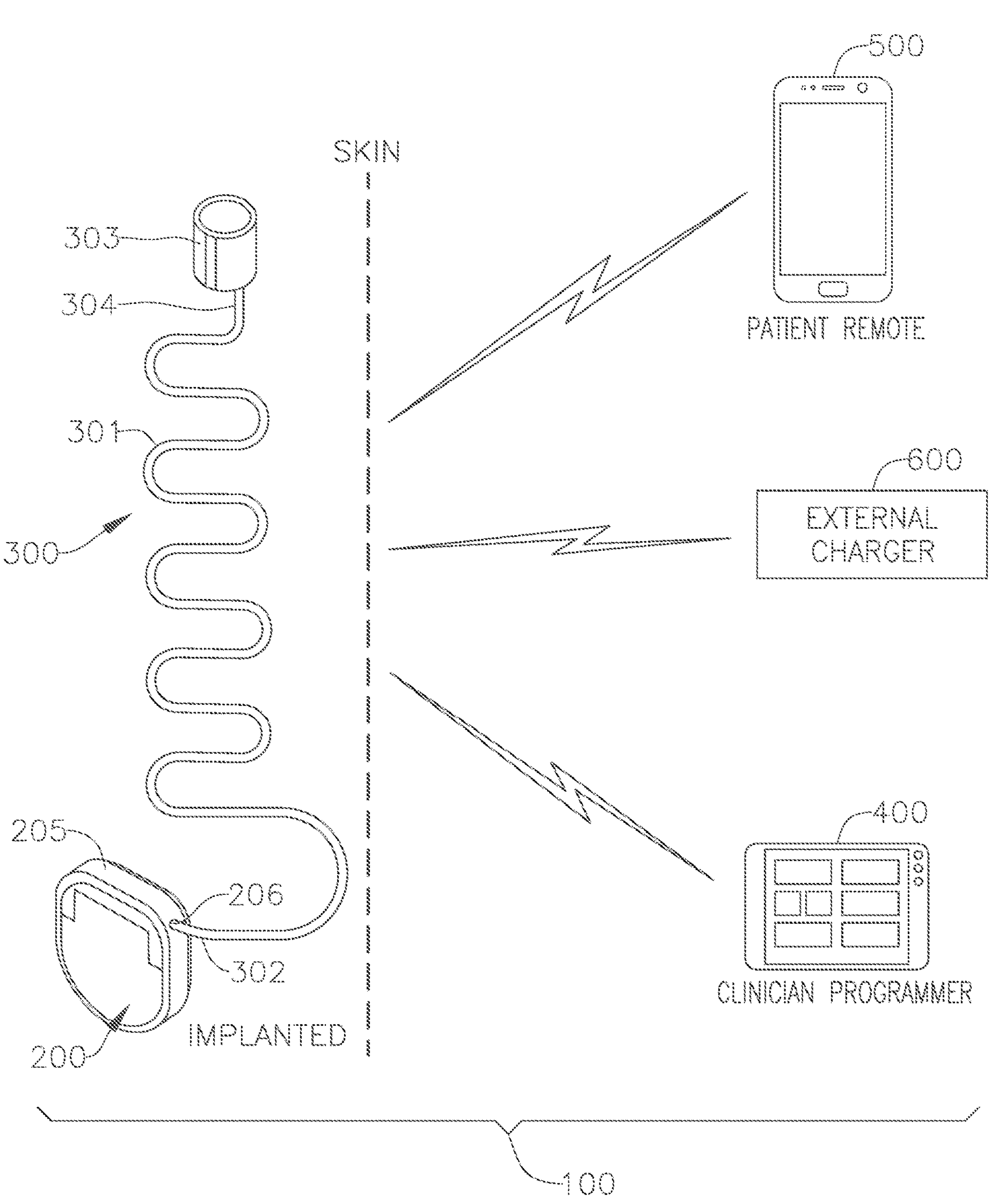
FIGS. 1A-1B are a perspective view and a schematic view, respectively, of an implantable pulse generator (IPG) according to one embodiment of the present disclosure.

The present disclosure relates to various embodiments of an implantable device configured to measure or determine one or more physiological indicators that may include physiological signals of an individual, such as heart rate and/or respiration rate. In one or more embodiments, the implantable device measures or determines the physiological signal(s) with an inertial sensing unit that includes one or more inertial sensors, such as a gyroscope and/or an accelerometer (e.g., an inertial measurement unit (IMU) including a gyroscope and an accelerometer), which may be less invasive than the electrocardiogram (EKG) method that utilizes implanted electrodes.

The implantable device is configured to receive the physiological signal(s) from the inertial sensor within a range of values (e.g., the acceleration measured by the accelerometer between a maximum acceleration and a minimum acceleration). The range of the inertial sensor may be minimized to increase the resolution and thus the sensitivity of the inertial sensor, which may enable detection of low-intensity physiological signals. The implantable device is also configured to dynamically increase the range (e.g., increase the minimum and maximum acceleration of the range) in response to the physiological signal reaching the maximum or the minimum (or reaching a threshold near the maximum or minimum values), which may be caused by bulk movements of the patient, such as movements during exercise or body roll while sleeping. In this manner, the implantable device is configured to prevent clipping of the physiological signal, which would otherwise introduce non-linearities and broad-spectrum noise that would prevent or inhibit analysis of the physiological signals of interest.

The implantable device is also configured to filter or separate out the physiological signal from signals that result from bulk patient motions, such as with a bandpass filter, and to stimulate and/or adjust the stimulation delivered by the implantable device to a nerve or a muscle of the patient in response to the physiological signal(s).

The terminology utilized herein is for the purpose of describing particular embodiments only and is not intended to be limiting of the present disclosure. As utilized herein, the singular forms "a", "an" and "the" are intended to include the plural forms as well, unless the context clearly indicates otherwise. As utilized herein, the term "and/or" includes any and all combinations of one or more of the associated listed items.

It will be understood that, although the terms "first", "second", "third", etc., may be utilized herein to describe one or more suitable elements, components, regions, and/or sections, these elements, components, regions, and/or sections should not be limited by these terms. These terms are only utilized to distinguish one element, component, region, layer or section from another element, component, region, layer or section. Thus, a first element, component, region, or section discussed could be termed a second element, component, region, or section, without departing from the spirit and scope of the present disclosure.

It will be understood that when an element is referred to as being "on", "connected to", "coupled to", or "adjacent to" another element, it can be directly on, connected to, coupled to, or adjacent to the other element, or one or more intervening element(s) may be present. In contrast, when an element is referred to as being "directly on," "directly connected to", "directly coupled to", or "immediately adjacent to" another element, there are no intervening elements present.

As utilized herein, the term "substantially" and similar terms are utilized as terms of approximation and not as terms of degree, and are intended to account for the inherent deviations in measured or calculated values that would be recognized by those of ordinary skill in the art. Also, the terms "about," "approximately," and similar terms, when utilized herein in connection with a numerical value or a numerical range, are inclusive of the stated value and refer to within an acceptable range of deviation for the particular value as determined by one of ordinary skill in the art, considering the measurement in question and the error associated with measurement of the particular quantity (e.g., the limitations of the measurement system).

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Example embodiments of the present disclosure will now be described with reference to the accompanying drawings. In the drawings, the same or similar reference numerals refer to the same or similar elements throughout. As utilized herein, the utilize of the term "may," when describing embodiments of the present disclosure, refers to "one or more embodiments of the present disclosure."

Figure 1B:
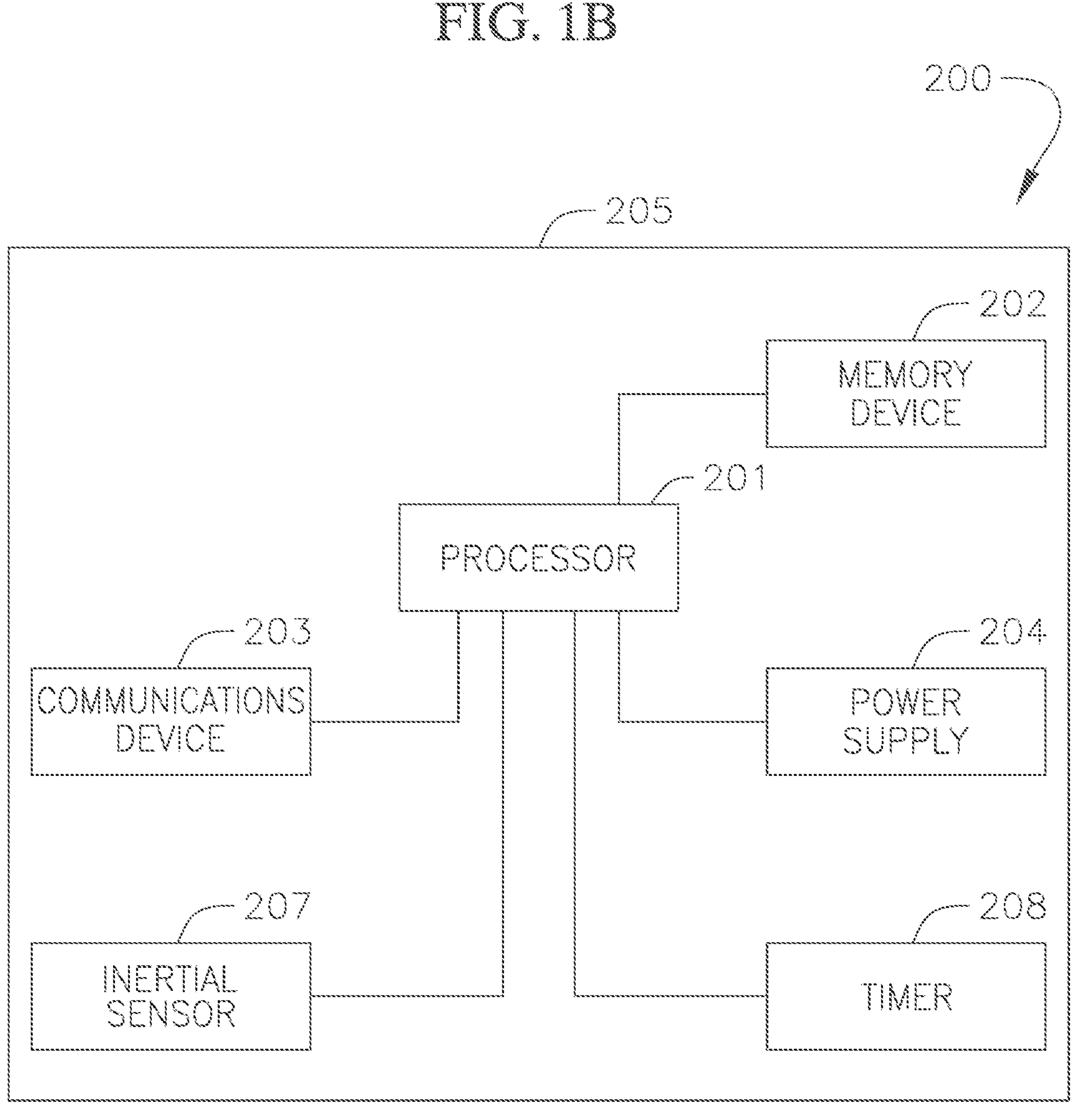

FIGS. 1A-1B are a perspective view and a schematic block diagram, respectively, of a stimulation system 100 configured to treat a patient via electrical stimulation, such as neurostimulation, cardiac stimulation, or spinal cord stimulation according to one embodiment of the present disclosure. The stimulation system 100 may include an implantable pulse generator (IPG) 200, and an implantable lead system 300 coupled to the IPG 200, implanted in a patient. In the illustrated embodiment, the implantable lead system 300 includes at least one electrical lead 301 having a proximal end 302 coupled to the IPG 200, and an electrode 303 coupled to a distal end 304 of the electrical lead 301 to periodically deliver an electric current pulse for a variety of therapeutic treatments for the patient, such as neurostimulation, cardiac stimulation, and/or spinal cord stimulation. The type or kind of the electrode 303 may be selected based on the location and the type of nerves stimulated (e.g., a cuff electrode to stimulate a nerve bundle, such as the hypoglossal nerve or the vagus nerve; a cardiac electrode to stimulate heart/myocardium; or a spinal cord lead, such as a paddle or a linear lead, to stimulate the spinal cord). The IPG 200 and the implantable lead system 300 may be implanted in any suitable locations in the patient depending on the therapeutic treatment delivered by the system 100. For example, the IPG 200 may be implanted in a subcutaneous pocket in the upper chest of the patient, and the electrical lead(s) 301 may extend from the IPG 200 through the superior vena cava such that the electrode(s) 303 are connected to the myocardium of the patient's heart. In one or more embodiments, the IPG 200 may be an obstructive sleep apnea (OSA) stimulator device implanted in a subcutaneous pocket in the upper chest of the patient, and the electrical lead(s) 301 may extend from the IPG 200 such that the electrode(s) 303 are connected to one or more of the patient's upper airway dilator muscles.

In the illustrated embodiment, the stimulation system 100 also includes a clinician programmer (CP) device 400 and a patient remote (PR) device 500 each electronically coupled to (i.e., in wireless RF communication with) the IPG 200, and an external charger 600 configured to charge the IPG 200 via inductive coupling.

With reference now to the embodiment illustrated in FIG. 1B, the IPG 200 includes a processor (e.g., a processing circuit) 201, a non-volatile memory device 202 (e.g., flash memory, or read-only memory (ROM), such as programmable read-only memory (PROM) or erasable programmable read-only memory (EPROM)), a communications device 203 (e.g., a receiver and a transmitter, or a transceiver), and a power supply 204 (e.g., a primary battery or an inductively chargeable rechargeable battery). The communications device 203 provides wireless communication links through the skin of the patient to the CP device 400 and the PR device 500. Wireless links may include Bluetooth™, Bluetooth Low Energy or other protocols with suitable authentication and encryption to protect patient data. The processor 201, the non-volatile memory device 202, the communications device 203, and the power supply 204 are in communication with each. Additionally, in the illustrated embodiment, the processor 201, the non-volatile memory device 202, the communications device 203, and the power supply 204 are housed in a housing or a case 205, and the proximal end(s) 302 of the electrical lead(s) 301 extend through opening(s) 206 in the case 205 and are connected to the power supply 204.

In the illustrated embodiment, the IPG 200 also includes an inertial sensing unit (or inertial sensor) 207 in the case 205 that is configured to determine (e.g., measure or calculate) physiological data, such as one or more physiological signals of the patient, such as respiration rate or heart rate. In one or more embodiments, the inertial sensing unit 207 may be an accelerometer and/or a gyroscope (e.g., the inertial sensing unit 207 may be an inertial measurement unit (IMU) including an accelerometer and a gyroscope). In one or more embodiments, the IPG 200 may include a plurality of inertial sensing units 207 configured to determine (e.g., measure or calculate) a plurality of physiological signals of the patient. In the illustrated embodiment, the IPG 200 also includes a timer 208 (e.g., a real-time clock (RTC)) in the case 205 that is configured to measure the passage of time. The inertial sensing unit 207 and the timer 208 are in communication with the processor 201.

As used herein, the term "processor" includes any combination of hardware, firmware, memory and software, employed to process data or digital signals. The hardware of a controller may include, for example, a microcontroller, application specific integrated circuits (ASICs), general purpose or special purpose central processors (CPUs), digital signal processors (DSPs), graphics processors (GPUs), and programmable logic devices such as field programmable gate arrays (FPGAs). In a processor, as utilized herein, each function is performed either by hardware configured, i.e., hard-wired, to perform that function, or by more general purpose hardware, such as a CPU, configured to execute instructions stored in a non-transitory storage medium or memory. A processor may contain two or more processors, for example, a processor may include two processors, an FPGA and a CPU, interconnected on a PCB.

Figure 2A:
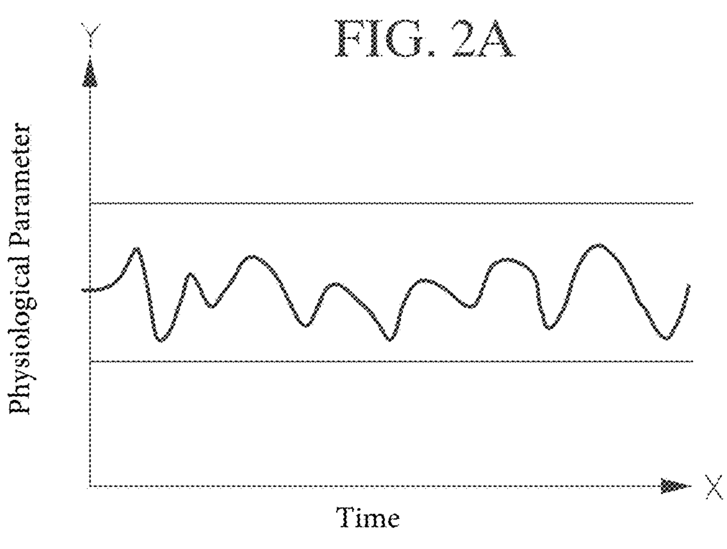
FIGS. 2A-2C are graphs depicting a physiological signal within an initial range/scale, the physiological signal clipping the initial range/scale, and the physiological signal within an enlarged range, respectively, according to one embodiment of the present disclosure.

In one or more embodiments, the memory device 202 includes computer-readable instructions (e.g., software code) which, when executed by the processor 201, cause the IPG 200 to capture (e.g., receive or record) the physiological signal(s) from the inertial sensing unit(s) 207 within an initial range between a maximum value and a minimum value (i.e., receive the physiological signal(s) from the inertial sensing unit(s) 207 within an initial scale). In one or more embodiments, the initial range may be relatively narrow such that the resolution is relatively high (e.g., the range may be a minimum range in which the physiological signals are anticipated to lie). For instance, in one or more embodiments in which the inertial sensing unit 207 is (or includes) an accelerometer, the range may be from −2G to +2G. FIG. 2A depicts the physiological signal, determined by the inertial sensor, within the initial range. Sampling the physiological signals at a relatively narrow range increases the resolution and sensitivity of the IPG 200, which may enable detection of low-intensity physiological signals, such as physiological signals when the patient is asleep. In one or more embodiments in which the IPG 200 includes two or more inertial sensing unit 207, the computer-readable instructions, when executed by the processor 201, cause the IPG 200 to capture the physiological signals through two or more channels (e.g., one channel for each physiological signal).

Figure 2B:
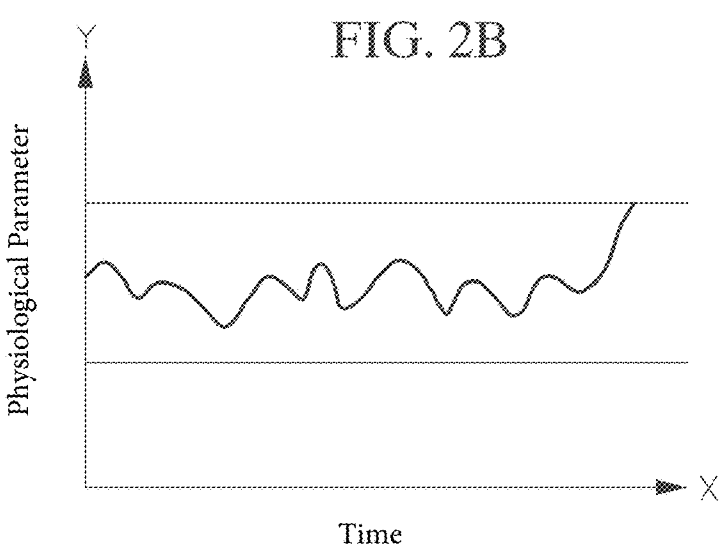
Figure 2C:
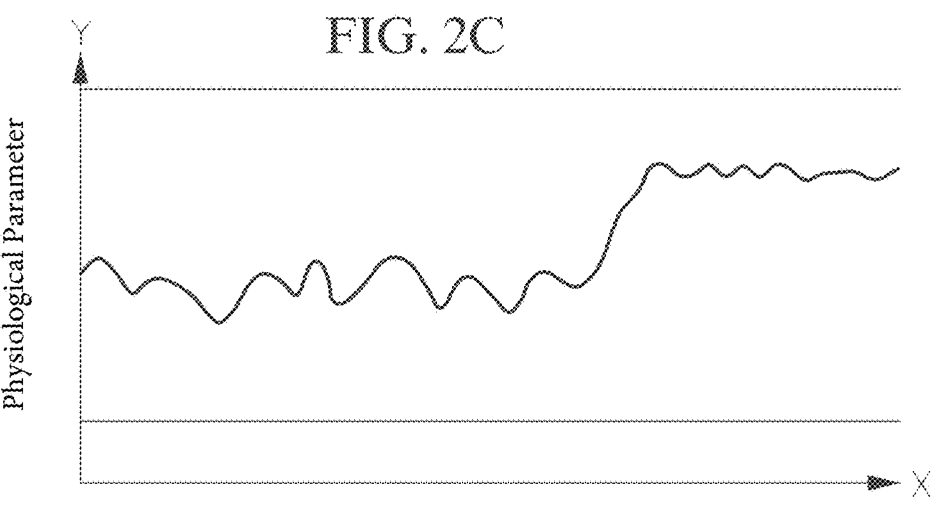

In one or more embodiments, the memory device 202 includes computer-readable instructions, when executed by the processor 201, cause the IPG 200 to dynamically increase the range in response to the physiological signal reaching (or approaching) the maximum value or the minimum value of the range. In one or more embodiments in which the IPG 200 includes two or more inertial sensing units 207 that gather physiological signals over two or more channels, the memory device 202 includes computer-readable instructions, when executed by the processor 201, cause the IPG 200 to dynamically increase the range for the channel(s) that clipped or approached clipping. In one or more embodiments, the instructions, when executed by the processor 201, cause the IPG 200 to increase the initial range to an enlarged range in response to the physiological signal reaching a threshold maximum value below the maximum value of the range (e.g., approximately 90% to approximately 99% of the maximum value) or reaching a threshold minimum value above the minimum value of the range (e.g., approximately 101% to approximately 110% of the minimum value). In one or more embodiments, the range may be adjustable in fixed increments (e.g., regular increments). For instance, in one or more embodiments in which the inertial sensing unit 207 is (or includes) an accelerometer, the range may increase from the initial range (e.g., −2G to +2G) to an enlarged range (e.g., −4G to +4G). The physiological signal may reach or approach the maximum or minimum value of the range due to bulk movements of the patient, such as when the patient works out or when the patient rolls over while sleeping. Increasing the range is configured to prevent a loss of signal information, which would otherwise occur if the signal reached the maximum or minimum value of the range. That is, increasing the range enables the physiological signal to be recovered. FIG. 2B depicts the physiological signal when it has clipped the first range (e.g., the physiological signal reached the maximum (or the maximum threshold) or the minimum (or the minimum threshold)), and FIG. 2C depicts the physiological signal when the range has been increased.

In one or more embodiments, the memory device 202 includes computer-readable instructions which, when executed by the processor 201, cause the IPG 200 to initiate a timer, utilizing the timer 208, in response to the initial range being increased to the enlarged range. That is, in one or more embodiments, the computer-readable instructions, when executed by the processor 201, cause the IPG 200 to initiate a timer in response to one of the physiological signals clipping (i.e., hitting the maximum or minimum value of the initial range) or approach clipping (i.e., reaching a threshold maximum value below the maximum value of the range or reaching a threshold minimum value above the minimum value of the range). In one or more embodiments, the timer may be 15 seconds or less (e.g., in a range from 5 seconds to 10 seconds). In one or more embodiments, the timer may be set based on maximum observed patient motion data.

In one or more embodiments, the memory device 202 includes computer-readable instructions which, when executed by the processor 201, cause the IPG 200 to reduce the enlarged range back to the initial range following expiration of the timer (e.g., 15 seconds or less). The timer is configured to account for the expected time that it will take for the bulk movements of the patient, such as rolling over while sleeping, to cease. Accordingly, reducing the range after the timer expires is configured to increase the resolution and sensitivity of the inertial sensor(s) while avoiding (or at least mitigating the risk of) the physiological signal clipping.

In one or more embodiments, the memory device 202 includes computer-readable instructions which, when executed by the processor 201, cause the IPG 200 to determine that the physiological signal is within a range narrower than the enlarged range. For example, in one or more embodiments in which the range may be adjusted in fixed increments (e.g., regular increments), the computer-readable instructions, when executed by the processor 201, cause the IPG 200 to determine that the physiological signal is within a range that it is at least one increment lower than the enlarged range. In one or more embodiments, the computer-readable instructions, when executed by the processor 201, cause the IPG 200 to determine that the physiological signal is within the initial range (e.g., the physiological signal has returned to the initial range after exceeding the initial range due to the bulk movement of the patient). As described above, reducing the range is configured to increase the resolution and sensitivity of the inertial sensing unit(s)) 207, which may enable detection of low-intensity physiological signals (e.g., physiological signals when the patient is asleep), while avoiding (or at least mitigating the risk of) the physiological signal clipping.

In one or more embodiments, the memory device 202 includes computer-readable instructions which, when executed by the processor 201, cause the IPG 200 to separate or differentiate the physiological signal from the portion of the signal attributed to the bulk movement of the patient (e.g., due to exercise or movement while sleeping). In one or more embodiments, the computer-readable instructions utilize a bandpass filter to separate the physiological signal from the portion of the signal attributed to the bulk movement of the patient. In one or more embodiments, the IPG 200 may utilize a software-based bypass filter or a physical bandpass filter device to separate the physiological signal from the portion of the signal attributed to the bulk movement of the patient. In one or more embodiments, the bandpass filter may have corner frequencies at 0.1 Hz and 0.5 Hz. In one or more embodiments, the bandpass filter has corner frequencies at 0.2 Hz and 50 Hz. In one or more embodiments, an adaptive filter may be utilized. For instance, in one or more embodiments in which the physiological signal measured by the inertial sensing unit 207 is respiration rate, an adaptive filter may be applied to adjust the corner frequencies based on the rise and fall time of the first 4 seconds (1 breath cycle) of the physiological signal.

In one or more embodiments, the memory device 202 includes computer-readable instructions which, when executed by the processor 201, cause the IPG 200 to stimulate a nerve and/or a muscle in the patient, via the one or more electrodes 303, based on the analysis of the one or more physiological signals. For instance, in one or more embodiments in which the IPG 200 is an obstructive sleep apnea (OSA) stimulator device and the inertial sensing unit 207 is configured to measure the respiration rate of the patient, the IPG 200 may apply electrical stimulation, via the one or more electrodes 303, to the upper airway dilator muscles of the patient in response to the respiration rate signal received by the inertial sensing unit 207 indicating that sleep apnea is occurring. In one or more embodiments in which the IPG 200 is a Vagus nerve stimulation (VNS) device and the inertial sensing unit 207 is configured to measure the heart rate of the patient, the IPG 200 may apply electrical stimulation, via the one or more electrodes 303, to the patient's Vagus nerve or hypoglossal nerve to shorten or lessen the severity of a possible seizure in response to analysis of the heart rate signal indicating ictal tachycardia is occurring.

Figure 3:
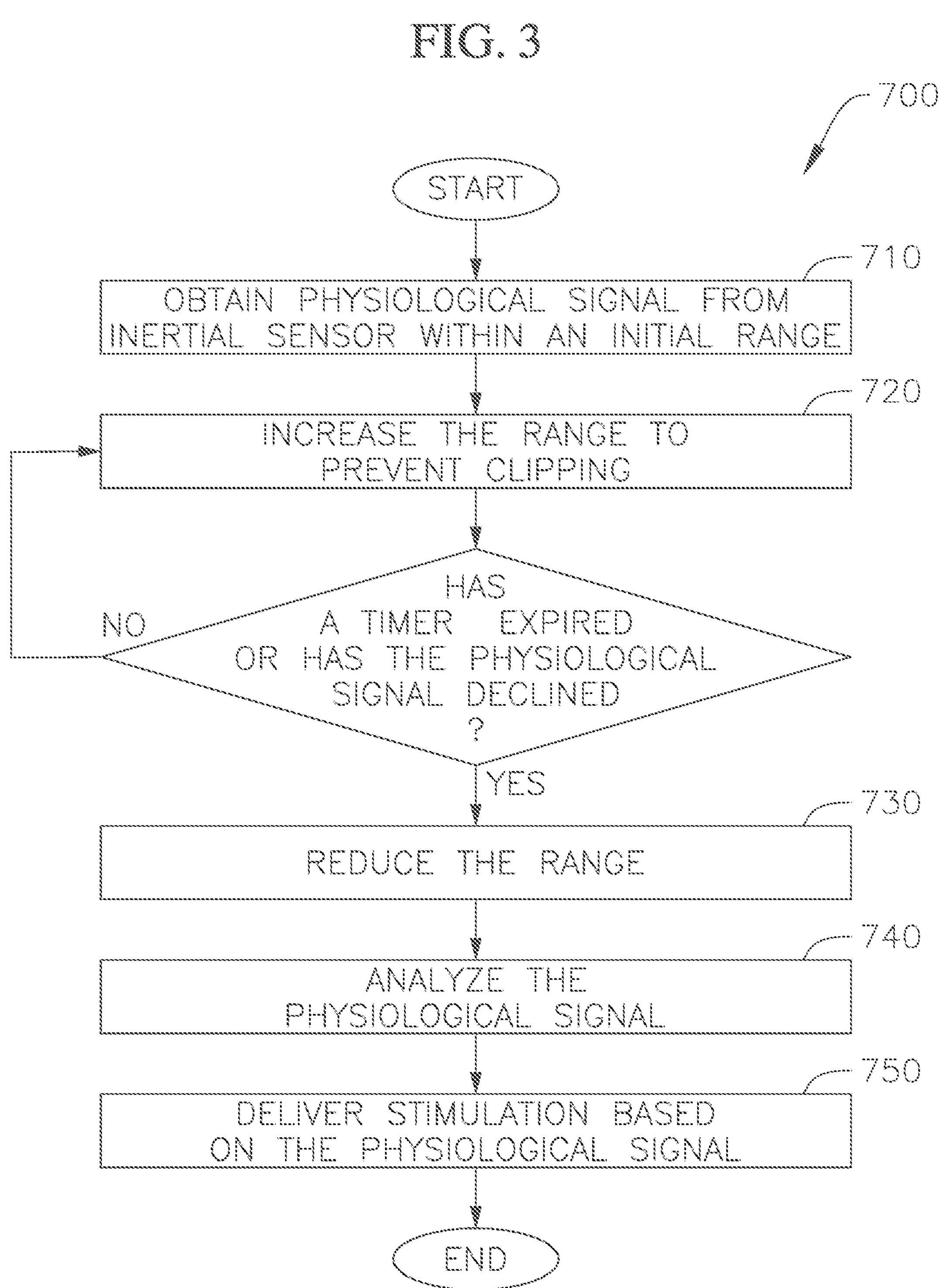
FIG. 3 is a flowchart is a method of operating an implantable medical device implanted in a patient according to one embodiment of the present disclosure.

FIG. 3 depicts a flowchart illustrating tasks of a method 700 of operating a medical device implanted in a patient. The medical may be an implantable pulse generator (IPG) implanted in a subcutaneous pocket in the upper chest of the patient. The medical device may be the IPG 200 and the implantable lead system 300 described above with reference to FIGS. 1A-1B.

In the illustrated embodiment, the method 700 includes a task 710 of obtaining (e.g., receiving or recording) physiological data, such as at least one physiological signal or indicator, from at least one inertial sensing unit (or inertial sensor) of the implantable medical device. The physiological signal obtained in task 710 may be, for example, a respiration signal or a heart rate signal. The physiological signal obtained in task 710 is within an initial range (i.e., an initial range between an initial minimum and an initial maximum). In one or more embodiments, the initial range may be a relatively narrow range (e.g., a minimum range) that is intended to encompass the fully physiological signal during normal operation. As described above, the relatively narrow initial range increases (e.g., maximizes) the resolution and thus the sensitivity of the implantable device, which may enable detection of low-intensity physiological signals, such as physiological signals when the patient is asleep.

In one or more embodiments, the method 700 also includes a task 720 of increasing the range from the initial range to an enlarged range (e.g., a maximum that is greater than the initial maximum and a minimum that is lower than the initial minimum) in response to the physiological signal reaching the maximum value or the minimum value of the range. In this manner, the task 720 is configured to prevent the physiological signal from clipping, which would otherwise result in the loss of signal information. For instance, the task 720 of increasing the range may be in response to the physiological signal reaching the maximum value of the initial range (or reaching a threshold maximum value below the maximum value of the range, such as approximately 90% to approximately 99% of the maximum value) or reaching the minimum value of the initial range (or reaching a threshold minimum value above the minimum value of the range, such as approximately 101% to approximately 110% of the minimum value). As described above, increasing the range is configured to prevent a loss of signal information, which would otherwise occur if the signal reached the maximum or minimum value of the range. In one or more embodiments, the task 720 may include increasing the range in fixed increments (e.g., regular increments). For instance, in one or more embodiments in which the inertial sensing unit is (or includes) an accelerometer, the task may include increasing from an initial range of −2G to +2G to a range from −4G to +4G.

In one or more embodiments, the method 700 also includes a task 730 of reducing the range (e.g., reducing the enlarged range back to the initial range). The task 730 of reducing the range may be performed in response to a timer expiring. The timer may have been initiated immediately after the task of increasing the range or simultaneously with the task of increasing the range. In one or more embodiments, the timer may be in a range from approximately 5 seconds to approximately 15 seconds. In one or more embodiments, the task 730 of reducing the range may be performed in response to the physiological signal dropping from within the enlarged range to a narrower range. In one or more embodiments, the task 730 of reducing the range may be performed in response to both the timer expiring and the signal analysis indicating that the physiological signal has dropped from within the enlarged range to within a narrower range. The physiological signal may drop once the bulk movement of the patient, such as exercising or rolling over while sleeping, has ceased.

In one or more embodiments, the method 700 also includes a task 740 of analyzing the physiological signal. In one or more embodiments, the task 740 of analyzing the physiological signal includes separating or differentiating the physiological signal from the portion of the signal attributed to the bulk movement of the patient (e.g., due to exercise or movement while sleeping). In one or more embodiments, the task 740 includes utilizing a bandpass filter (e.g., a software-based bandpass filter or a physical bandpass filter device) to separate the physiological signal from the portion of the signal attributed to the bulk movement of the patient.

In one or more embodiments, the method 700 also includes a task 750 of stimulating the patient based on the analysis of the physiological signal in task 740. The task 750 may include applying electrical stimulation, via the one or more electrodes, to the upper airway dilator muscles of the patient in response to the respiration rate signal received by the inertial sensing unit indicating that sleep apnea is occurring. In one or more embodiments, the task 750 may include applying electrical stimulation, via the one or more electrodes, to the patient's Vagus nerve to shorten or lessen the severity of a possible seizure in response to analysis of the heart rate signal indicating ictal tachycardia is occurring.

The implantable pulse generator and/or any other relevant devices or components according to embodiments of the present invention described herein may be implemented utilizing any suitable hardware, firmware (e.g., an application-specific integrated circuit), software, or a combination of software, firmware, and hardware. For example, the various components of the device may be formed on one integrated circuit (IC) chip or on separate IC chips. Further, the various components of the device may be implemented on a flexible printed circuit film, a tape carrier package (TCP), a printed circuit board (PCB), or formed on one substrate. Further, the various components of the device may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the scope of the exemplary embodiments of the present invention.

Although some embodiments of the present disclosure are disclosed herein, the present disclosure is not limited thereto, and the scope of the present disclosure is defined by the appended claims and equivalents thereof.

What is claimed is:

1. A medical device comprising:
- an implantable pulse generator comprising:
  - a processor:
  - a non-volatile memory device coupled to the processor;
  - a power supply coupled to the processor; and
  - an inertial sensing unit coupled to the processor, the inertial sensing unit being configured to measure one or more physiological indicators of a patient; and
- an implantable lead system comprising:
  - at least one electrical lead coupled to the power supply of the implantable pulse generator; and
  - at least one electrode at a distal end of the at least one electrical lead,
- wherein the non-volatile memory device comprises instructions stored therein which, when executed by the processor, cause the implantable pulse generator to:
  - set an initial range of the inertial sensing unit below a maximum range of the inertial sensing unit to increase a resolution and a sensitivity of the inertial sensing unit to low-intensity physiological signals;
  - receive the one or more physiological indicators, measured from the inertial sensing unit at a first time period, the one or more physiological indicators being within the initial range;
  - increase the initial range to an enlarged range in response to at least one of the one or more physiological indicators reaching a threshold maximum value or a threshold minimum value of the initial range to prevent clipping;
  - receive the one or more physiological indicators, measured from the inertial sensing unit at a second time period after the first time period, within the enlarged range,
  - analyze the one or more physiological indicators within the enlarged range and/or within the initial range, and
  - deliver stimulation to the patient through the at least one electrode in response to the one or more physiological indicators within the enlarged range and/or within the initial range.

2. The implantable pulse generator of claim 1, wherein the instructions, when executed by the processor, further cause the implantable pulse generator to distinguish the one or more physiological indicators from broad-spectrum noise in the enlarged range utilizing a bandpass filter.

3. The implantable pulse generator of claim 2, wherein the bandpass filter has corner frequencies at 0.1 Hz and 0.5 Hz.

4. The implantable pulse generator of claim 2, wherein the bandpass filter has corner frequencies at 0.2 Hz and 50 Hz.

5. The implantable pulse generator of claim 2, wherein the bandpass filter is an adaptive bandpass filter.

6. The implantable pulse generator of claim 1, wherein the at least one inertial sensing unit comprises an accelerometer.

7. The implantable pulse generator of claim 6, wherein the initial range is −2G to +2G.

8. The implantable pulse generator of claim 7, wherein the enlarged range is −4G to +4G.

9. The implantable pulse generator of claim 1, wherein the at least one inertial sensing unit comprises a gyroscope.

10. The implantable pulse generator of claim 1, wherein the one or more physiological indicators comprise respiration rate.

11. The implantable pulse generator of claim 10, wherein the instructions, when executed by the processor, cause the implantable pulse generator to deliver electrical stimulation through the at least one implantable lead to upper airway dilator muscles of the patient.

12. The implantable pulse generator of claim 1, wherein the one or more physiological indicators comprise heart rate.

13. The implantable pulse generator of claim 10, wherein the instructions, when executed by the processor, cause the implantable pulse generator to deliver electrical stimulation through the at least one implantable lead to the patient's Vagus nerve or hypoglossal nerve.

14. The implantable pulse generator of claim 1, wherein the at least one inertial sensing unit comprises a plurality of inertial sensing units configured to measure a plurality of the physiological indicators of the patient.

15. The implantable pulse generator of claim 1, wherein the instructions, when executed by the processor, further cause the implantable pulse generator to:

initiate a timer in response to initial range being increased to the enlarged range; and decrease the enlarged range to the initial range in response to the timer expiring.

16. The implantable pulse generator of claim 15, wherein the timer is in a range from approximately 5 seconds to approximately 15 seconds.

17. The implantable pulse generator of claim 1, wherein the instructions, when executed by the processor, further cause the implantable pulse generator to decrease the initial range to a narrower range less than the initial range in response to at least one of the one or more physiological indicators being within the narrower range.

18. The implantable pulse generator of claim 1, wherein the instructions, when executed by the processor, cause the implantable pulse generator to adjust the initial range in regular increments.

19. A method of providing stimulation to a patient, the method comprising:

setting an initial range of an inertial sensing unit of an implantable pulse generator implanted in the patient below a maximum range of the inertial sensing unit to increase a resolution and a sensitivity of the inertial sensing unit to low-intensity physiological signals;

measuring, with the inertial sensing unit of the implantable pulse generator implanted in the patient, one or more physiological indicators of the patient at a first time period, the one or more physiological indicators being within the initial range;

increasing the initial range to an enlarged range in response to at least one of the one or more physiological indicators reaching a threshold maximum value or a threshold minimum value of the initial range to prevent clipping;

measuring, with the inertial sensing unit, the one or more physiological indicators of the patient at a second time period after first time period, the one or more physiological indicators being within the enlarged range;

receiving the one or more physiological indicators within the enlarged range;

analyzing the one or more physiological indicators within the enlarged range and/or the initial range; and delivering stimulation to the patient, through at least one implantable lead coupled to the implantable pulse generator, in response to the one or more physiological indicators within the enlarged range and/or the initial range.

20. The method of claim 19, wherein the analyzing the one or more physiological indicators comprises filtering the one or more physiological indicators from broad-spectrum noise in the enlarged range utilizing a bandpass filter.

21. The method of claim 20, wherein the bandpass filter has corner frequencies at 0.1 Hz and 0.5 Hz.

22. The method of claim 20, wherein the bandpass filter has corner frequencies at 0.2 Hz and 50 Hz.

23. The method of claim 20, wherein the bandpass filter is an adaptive bandpass filter.

24. The method of claim 19, wherein the at least one inertial sensing unit comprises an accelerometer.

25. The method of claim 19, wherein the initial range is −2G to +2G.

26. The method of claim 25, wherein the enlarged range is −4G to +4G.

27. The method of claim 19, wherein the at least one inertial sensing unit comprises a gyroscope.

28. The method of claim 19, wherein the one or more physiological indicators comprise respiration rate.

29. The method of claim 28, wherein the delivering stimulation comprises delivering electrical stimulation through the at least one implantable lead to upper airway dilator muscles of the patient.

30. The method of claim 19, wherein the one or more physiological indicators comprise heart rate.

31. The method of claim 30, wherein the delivering stimulation comprises delivering electrical stimulation through the at least one implantable lead to the patient's Vagus nerve or hypoglossal nerve.

32. The method of claim 19, wherein the measuring comprises measuring a plurality of physiological indicators of the patient.

33. The method of claim 19, further comprising:

initiating a timer in response to the increasing of the initial range to the enlarged range; and decreasing the enlarged range to the initial range in response to the timer expiring.

34. The method of claim 33, wherein the timer is in a range from approximately 5 seconds to approximately 15 seconds.

35. The method of claim 19, further comprising decreasing the initial range to a narrower range less than the initial range in response to at least one of the one or more physiological indicators being within the narrower range.

36. The method of claim 19, further comprising adjusting, by the implantable pulse generator, the initial range in regular increments.

* * * * *